(12) United States Patent
Tretjak et al.

(10) Patent No.: US 12,098,123 B2
(45) Date of Patent: Sep. 24, 2024

(54) POLYMER GRADE ACRYLIC ACID PRODUCTION

(71) Applicant: ARKEMA FRANCE, Colombes (FR)

(72) Inventors: Serge Tretjak, Saint Avold cedex (FR); Veronique Scharff, Colombes cedex (FR); Aurelien Huve, Saint Avold cedex (FR)

(73) Assignee: Arkema France, Colombes (FR)

( * ) Notice: Subject to any disclaimer, the term of this patent is extended or adjusted under 35 U.S.C. 154(b) by 494 days.

(21) Appl. No.: 17/442,335

(22) PCT Filed: Mar. 20, 2020

(86) PCT No.: PCT/FR2020/050607
§ 371 (c)(1),
(2) Date: Sep. 23, 2021

(87) PCT Pub. No.: WO2020/201661
PCT Pub. Date: Oct. 8, 2020

(65) Prior Publication Data
US 2022/0169589 A1 Jun. 2, 2022

(30) Foreign Application Priority Data
Apr. 2, 2019 (FR) ..................................... 1903519

(51) Int. Cl.
*C07C 51/44* (2006.01)
*C07C 57/04* (2006.01)
(52) U.S. Cl.
CPC .............. *C07C 57/04* (2013.01); *C07C 51/44* (2013.01)

(58) Field of Classification Search
CPC ................................ C07C 57/04; C07C 51/44
See application file for complete search history.

(56) References Cited

U.S. PATENT DOCUMENTS

| | | |
|---|---|---|
| 3,725,208 A | 4/1973 | Maezawa et al. |
| 5,504,247 A | 4/1996 | Saxer et al. |
| 7,393,976 B2 | 7/2008 | Benderly et al. |
| 8,242,308 B2 | 8/2012 | Ho et al. |
| 8,530,700 B2 | 9/2013 | Ho et al. |

(Continued)

FOREIGN PATENT DOCUMENTS

| | | |
|---|---|---|
| EP | 1110940 A2 | 6/2001 |
| JP | 5466515 Y1 | 3/1971 |

(Continued)

OTHER PUBLICATIONS

JPS46-006515, BP Chemicals Limited, Purifying acrylic acid, 3 pages, English translation (Year: 1971).*

*Primary Examiner* — Yate' K Cutliff
(74) *Attorney, Agent, or Firm* — Debodhonyaa Sengupta

(57) ABSTRACT

The invention relates to the purification of an acrylic acid comprising aldehyde compounds in a low content, according to a distillation process in a distillation unit in the absence of chemical reagent for treating the aldehydes, producing a stream of polymer-grade acrylic acid which is withdrawn through a side outlet of the distillation unit. The invention makes it possible to eliminate the use of a product classified as CMR in the manufacture of polymer-grade acrylic acid from a technical-grade acrylic acid, and thus meets the HSE requirements for industrial plants.

10 Claims, 2 Drawing Sheets

(56) References Cited

U.S. PATENT DOCUMENTS

| | | | |
|---|---|---|---|
| 8,748,545 B2 | 6/2014 | Devaux et al. | |
| 9,371,261 B2 | 6/2016 | Fauconet | |
| 10,112,885 B2 | 10/2018 | Decourcy | |
| 10,845,222 B2 | 11/2020 | Lais et al. | |
| 11,214,534 B2 | 1/2022 | Hoyme et al. | |
| 2009/0253934 A1 | 10/2009 | Ho et al. | |
| 2012/0226074 A1 | 9/2012 | Ho et al. | |
| 2013/0165690 A1 | 6/2013 | Fauconet et al. | |
| 2017/0174604 A1 | 6/2017 | Decourcy | |
| 2018/0266857 A1 | 9/2018 | Lais et al. | |
| 2020/0115311 A1* | 4/2020 | Fauconet | C07C 51/215 |

FOREIGN PATENT DOCUMENTS

| | | | | |
|---|---|---|---|---|
| JP | S46-6515 | * | 12/1971 | C07C 57/07 |
| JP | S466515 A | | 12/1971 | |
| WO | WO-2018185423 A1 | * | 10/2018 | B01D 3/141 |

* cited by examiner

[Fig. 1]
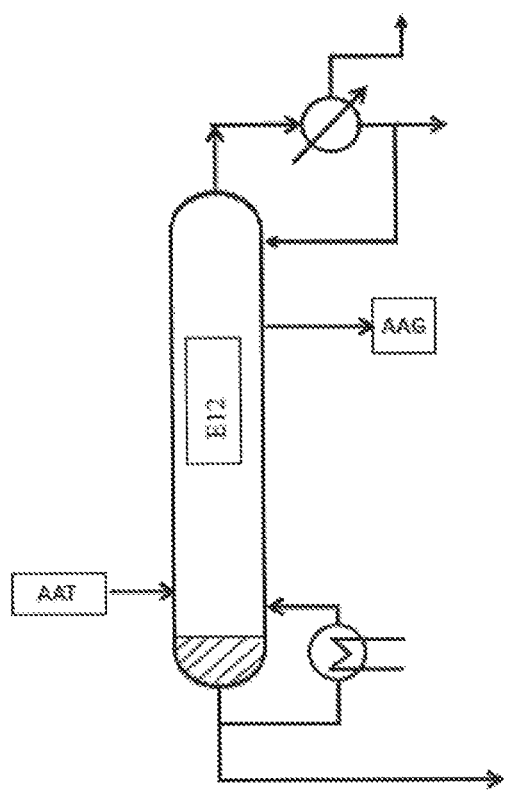

[Fig. 2]
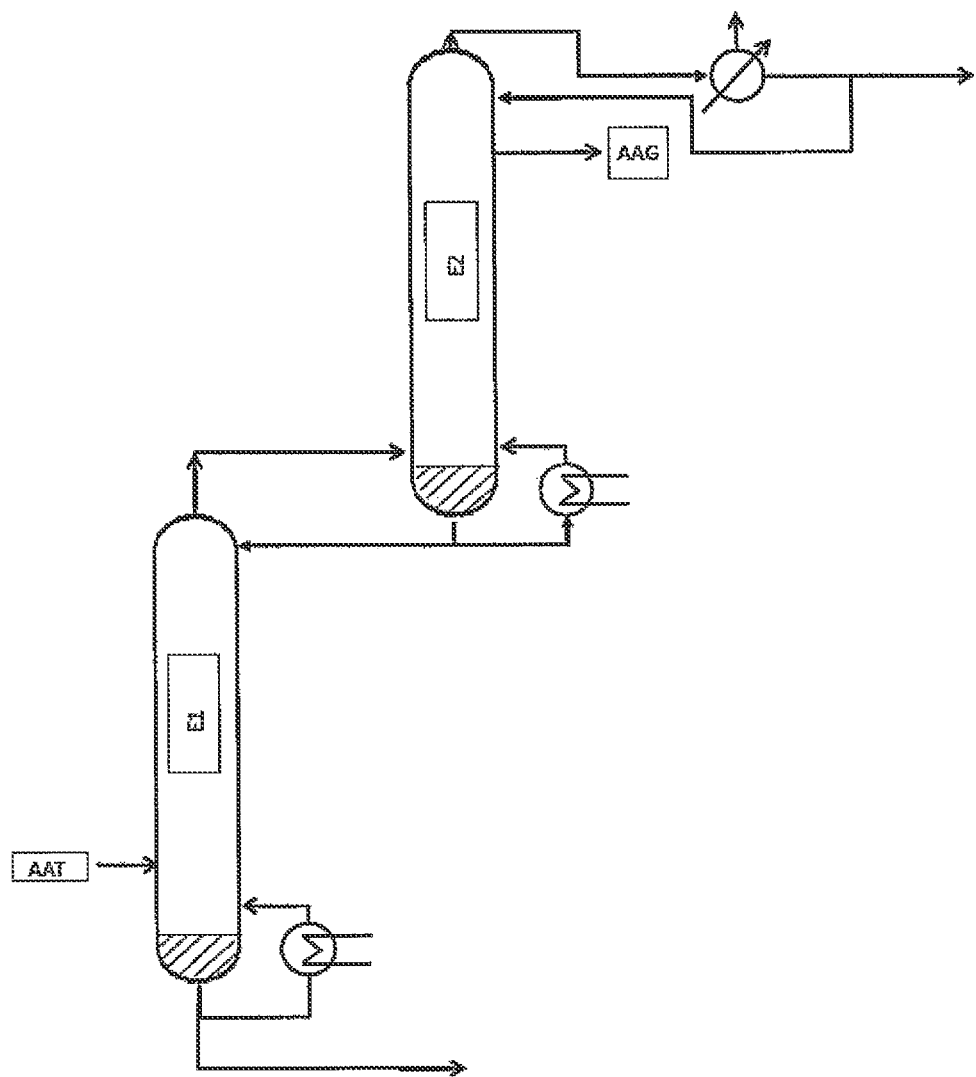

POLYMER GRADE ACRYLIC ACID PRODUCTION

CROSS-REFERENCE TO RELATED APPLICATIONS

This application is a national stage application under 35 U.S.C. § 371 of PCT/FR2020/050607, filed Mar. 20, 2020 which claims benefit to application FR19.03519, filed Apr. 2, 2019.

TECHNICAL FIELD

The present invention relates to the production of polymer-grade acrylic acid, commonly referred to as glacial acrylic acid.

TECHNICAL BACKGROUND AND TECHNICAL PROBLEM

Processes for producing acrylic acid from propylene carry out, after leaving the propylene oxidation reactors, various purification steps which may differ in their sequence according to the process:
  removal of the noncondensable gases and most of the very light compounds, in particular acrolein, an intermediate in the synthesis of acrylic acid (crude AA),
  dehydration removing water and formaldehyde (dehydrated AA),
  removal of the light compounds (in particular acetic acid), then
  removal of the heavy compounds (technical AA).

Each step thus produces an acrylic acid quality which differs in the content of residual impurities which will remain therein. These impurities, owing to the amounts thereof and the nature thereof, will limit the acrylic acid obtained to one particular type of application. When acrylic acid is intended for use in polymerization processes carried out in various forms, in bulk, in solution, in suspension, or in emulsion, the quality of the acrylic acid (AA), i.e. its content of various impurities will play a big part in the subsequent polymerization processes. The manufacturers manufacturing this acrylic acid then bring into play additional purification steps in order to convert the technical acrylic acid (TAA) into "standard" acrylic acid which is usually referred to as glacial acrylic acid (GAA) or polymer-grade acrylic acid.

To achieve the glacial acrylic acid quality that makes it possible to synthesize high molecular weight polymers, it is particularly important to remove certain impurities in technical AA down to extremely low contents. These are in particular certain aldehydes, such as furfuraldehyde (or furfural), benzaldehyde or acrolein, or other impurities such as protoanemonin, compounds generated during the synthesis of acrylic acid, or else non-phenolic polymerization inhibitors such as phenothiazine, capable of having been introduced during the synthesis of acrylic acid. These compounds have a considerable effect on the reactivity of glacial AA when it is used in a polymerization reaction aimed at producing a high molecular weight polymer, by slowing down or inhibiting the reaction.

Thus, it will usually be a question of converting, by a purification operation such as distillation in the presence of a chemical agent or by a crystallization operation, a technical acrylic acid having a purity of greater than 98.5 wt %, and still containing heavy impurities such as aldehydes: Furfural: <0.05%; Benzaldehyde: <0.05%, Protoanemonin: <0.05%, into polymer-grade acrylic acid.

The latter can be characterized as follows:
  purity greater than 99.5 wt %,
  less than 0.05 wt % water,
  less than 0.075% acetic acid,
  furfural content<2 ppm,
  benzaldehyde content<2 ppm,
  protoanemonin content<2 ppm,
  a weight content of total aldehydes<10 ppm.

The processes for obtaining technical acrylic acid are well known. Thus, documents EP 2 066 613, WO 2015/126704, WO 2008/033687, based on a "solvent-free" technology, describe a process for recovering acrylic acid without using external water or an azeotropic solvent. This process uses two distillation columns to purify the cooled gaseous reaction mixture: a) a dehydration column, b) a finishing column supplied with a portion of the bottom stream from the dehydration column. Obtaining a glacial acrylic acid using the solvent-free process as described in these patents cannot be envisaged in the context of the present invention. Specifically, the finishing column used would then have to separate the light products (water, acetic acid) from the acrylic acid stream, and also separate the heavy compounds (furfural, benzaldehyde) from this acrylic acid stream, in the same column. The number of separation stages and consequently Dual Flow trays then increases significantly, which would lead to a pressure drop and an increase in the temperature at the bottom of the column which is not compatible with the heat-sensitive nature of the acrylic acid.

In order to obtain glacial acrylic acid, documents EP 2 066 613 or WO 2008/033687 indicate that the technical acrylic acid obtained by their process can be subjected to an additional treatment by fractional crystallization, as described in patent U.S. Pat. No. 5,504,247 by Sulzer, or in document WO 2011/010035 by the Applicant Company relating to the production of polymer-grade acrylic acid of renewable origin. This technology nevertheless requires an investment cost and an operating cost (electricity consumption) which may prove to be greater than a distillation process.

It is also possible to obtain glacial acrylic acid by an additional distillation operation combined with a chemical treatment for removing the aldehydes. Among the reagents that can be used, use may be made of amines, and more particularly compounds of the hydrazine family, as described in U.S. Pat. Nos. 3,725,208 or 7,393,976. Generally, these compounds can be used as is or in the form of salts or hydrates thereof.

Document WO 2017/050583 supplements the solvent-free processes described in WO 2015/126704 and WO 2008/033687 by proposing the addition of an aldehyde treatment step using a chemical agent, carried out in a purification section comprising a dehydration column, and a finishing column (or purification column), preferably inside said purification section, or alternatively in an additional purification section by distillation with one or two distillation columns, and making it possible to result in glacial acrylic acid quality.

The chemical treatments which are described in the prior art all have the drawback of generating water during the reaction of the aldehydes with the chemical reagent.

The presence of water in the acrylic acid can be detrimental to the manufacture of polymers in a non-aqueous medium. For this reason, it may be advantageous to carry out this aldehyde chemical treatment operation during a distillation step aimed at removing the water and the light compounds at the top, before a step of distillation of the acrylic acid intended to separate the heavy compounds, as described for example in document WO 2010/031949. However, this method requires the use of at least two distillation columns.

Another drawback of the chemical treatment for removing aldehydes by amino compounds is their reactivity toward the acrylic acid itself, which leads to a significant reduction in the stability of the medium.

Despite the use of inhibitors conventionally used for the distillation of this monomer, polymer deposits are observed, particularly on the column plates and/or the hot wall of the boiler. The formation of these solid deposits quickly leads to problems of blockages or modification of heat exchanges which necessitate a shutdown of the plant for cleaning.

Another drawback of the processes using a chemical treatment of the aldehydes is the loss of acrylic acid in the residual stream obtained after separation of the purified AA. As the desired reactions of the chemical agent (for example hydrazine) with the aldehydes are not selective, a large excess of reagent relative to the aldehydes to be treated must be used, and the residual stream composed mainly of acrylic acid cannot be recycled or used as raw material for ester manufacture for example, owing to the presence of the reaction products of the reagent with the aldehydes and with the acrylic acid. This therefore constitutes a loss of acrylic acid recovery yield.

Finally, one of the major drawbacks of the chemical treatment of the aldehydes stems from the nature of the compounds generally used, such as hydrazine and derivatives thereof which are products classified as CMR (carcinogens 1B) or aminoguanidine or derivatives thereof which are also classified as CMR (reprotoxic 1B). It is obvious, for reasons of health, safety and environment (HSE), that the use of this type of substance should be avoided whenever possible in industrial plants. If this product is used, strict measures for containment, handling and management of the effluents in normal operation or in the event of a leak must be put in place in a draconian manner, resulting in a high operating cost.

More recently, in document WO 2018/185423, the use of a dividing-wall column as a purification/finishing column in a process for recovering acrylic acid using two distillation columns in the absence of external organic solvent was described. The particular configuration of the dividing-wall column, i.e. when the dividing wall is contiguous with the upper dome of the column in the top part, and not contiguous with the bottom of the column in the bottom part, makes it possible to improve the energy balance of the process while improving the technical quality of the acrylic acid recovered. The technical acrylic acid extracted at the top of the dividing-wall column can be subjected to an additional treatment by fractional crystallization, or by distillation optionally in the presence of a compound which reacts with the residual aldehydes, resulting in a polymer-grade acrylic acid quality. Owing to the improved technical quality, further purification to produce a polymer grade is simplified. Furthermore, under certain conditions of use of the dividing-wall column, it has been observed that a polymer-grade acrylic acid, meeting specifications relating to the residual content of aldehydes such as furfural or benzaldehyde, and of protoanemonin, can be extracted directly at the top of the dividing-wall column. Nevertheless, the use of a dividing-wall distillation column remains complex and specific. Indeed, the purification described in this document cannot be adapted, without significant modification, to the conventional processes for recovering acrylic acid using an external organic solvent such as those described in documents WO 10/031949 and WO 11/114051 relating to the synthesis of acrylic acid from glycerol.

Therefore, there remains a need to provide a method that is simple, rapid and easy to use for removing aldehydes, such as furfural and benzaldehyde and also acrolein, or other impurities such as protoanemonin, in a technical acrylic acid, leading to a polymer grade (or glacial) acrylic acid quality, without the intervention of a chemical agent for treating the aldehydes, or of expensive technology such as that using a dividing-wall distillation column.

The inventors have now discovered that this need could be met by a simple operation of distilling a technical acrylic acid, applied under particular conditions, and suitable irrespective of the quality of the technical acrylic acid or its production method.

Furthermore, it has become apparent to the inventors that this invention could be applied to acrylic acid produced from propylene and/or propane and also to acrylic acid derived from renewable raw materials.

SUMMARY OF THE INVENTION

The present invention relates to a process for manufacturing glacial acrylic acid from a technical acrylic acid comprising aldehyde compounds in a low content, said process consisting of a distillation carried out in a distillation unit in the absence of a chemical reagent for treating the aldehydes, producing a stream of polymer-grade acrylic acid which is withdrawn through a side outlet of the distillation unit, a stream comprising essentially light compounds being extracted at the top of the distillation unit, and a stream of technical acrylic acid comprising heavy compounds being recovered at the bottom of the distillation unit.

Advantageously, the process of the invention does not use a dividing-wall distillation column.

According to a first embodiment of the invention, the distillation unit comprises a single distillation column E12 equipped with a sidestream drawoff. Generally; the column E12 comprises a number of theoretical plates of between 15 and 30, preferably between 20 and 25.

According to a second embodiment of the invention, the distillation unit comprises a first distillation column E1, in which the stream generated at the top feeds a second distillation column E2 equipped with a sidestream drawoff. Generally, each of the columns E1 and E2 comprises a number of theoretical plates of between 8 and 15, preferably between 10 and 12.

According to these two embodiments; the acrylic acid subjected to the process according to the invention is a technical grade acrylic acid with a weight content of greater than 99.5%, comprising a low content of aldehydes such as furfural, benzaldehyde and acrolein, and which may comprise light compounds such as acrolein, acetic acid or water; the process according to the invention makes it possible to produce a stream of purified acrylic acid that meets the criteria of high quality allowing its use in the manufacture of high molecular weight acrylic polymers, in the absence of addition of a chemical compound for treating the aldehydes.

In particular, the polymer-grade acrylic acid obtained according to the process of the invention can be characterized as follows:
   weight content of total aldehydes (furfural, benzaldehyde, acrolein): <10 ppm, preferably <4 ppm,
   content of protoanemonin: <2 ppm,
   weight content of water: <0.1% preferably <0.05%,
   weight content of acetic acid: <0.1%, preferably <0.08%.

The invention thus makes it possible to overcome the drawbacks of the prior art processes, by eliminating the use of a product classified as CMR in the manufacture of polymer-grade acrylic acid from a technical grade acrylic acid. As a result, the formation of water related to reactions between the amino compounds such as hydrazine and the aldehydes or unsaturated acids is avoided, and the following problems due to the use of a chemical reagent do not occur.

Moreover, the residual product resulting from the distillation of technical acrylic acid with a view to obtaining polymer-grade acrylic acid, recovered at the bottom of the distillation unit, can be advantageously recycled to an esterification plant manufacturing $C_1$-$C_8$ acrylic esters, without additional purification which would be essential if an agent for the chemical treatment of the aldehydes was used.

According to certain particular embodiments, the invention also has one or, preferably, several of the advantageous features listed below:

- The distillation unit comprises at least one top reflux, in particular a reflux at the top of the distillation column E12 or the column E2 equipped with a sidestream drawoff.
- The distillation unit comprises, at the top, a condenser which may be a complete or partial condenser, which makes it possible to at least partially condense the distilled stream rich in light compounds. The condensed stream is sent back, at least in part, to the top of column E12 or E2 which are equipped with a sidestream drawoff. The uncondensed portion is removed, for example by sending it to an incinerator before final discharge to the atmosphere, or can be recycled upstream of the process, for example to the column for the absorption of acrylic acid from the reaction gases. The portion of the condensed stream which is not recycled as reflux in the column can be removed, or preferably recycled upstream of the purification process, or be used for the manufacture of acrylic esters.
- The sidestream drawoff of acrylic acid can be carried out in the gas phase or in the liquid phase. It is preferably carried out in the liquid phase in order to limit the amount of acrolein present therein.
- The sidestream drawoff comprises a condenser which cools the acrylic acid to a temperature of the order of 30° C. before storage.
- At least one phenolic polymerization inhibitor is introduced into the condenser associated with the sidestream drawoff, preferentially hydroquinone methyl ether (MEHQ), in an amount suitable for protecting the condensed stream from polymerization in the condenser, in the storage tank and during transport before use of the acrylic acid, and that meets the polymerization reactivity requirements.
- The sidestream drawoff is preferably carried out in the first third of the top of the column E12 or E2.
- At least one phenolic polymerization inhibitor, preferably MEHQ, is introduced at the top of the columns E2 and E12 upstream of the condenser, so as to prevent polymer formation during the condensation of the distilled gas mixture and in the column, owing to the presence of this inhibitor in the liquid reflux sent back to the top of the column.
- In addition, polymerization inhibitors, in particular non-phenolic polymerization inhibitors, can be sent alone or in combination, to a plate located under the sidestream drawoff of columns E2 or E12 and/or at the top of column E1. The inhibitors used are those employed by a person skilled in the art for the purification of acrylic acid.
- Air or lean air is injected at the bottom of the distillation unit, in column E12 or E1, preferably in a volume proportion of 0.1% to 0.5% oxygen relative to the total flow rate of distilled AA.
- The weight ratio between the stream withdrawn as a sidestream and the feed stream is between 60% and 90%, preferably between 70% and 80%.
- The weight ratio between the stream withdrawn as bottoms and the feed stream is between 10% and 40%, preferably between 20% and 30%.
- The stream recovered at the bottom of the distillation unit is advantageously recycled to an esterification unit without additional treatment.
- The reflux ratio which can be defined as the rate of recycling from the top of the column to the column, relative to that of sidestream drawoff, is between 1.5 and 4, preferably between 2 and 3, for example is equal to 2.5. Under these conditions, it is possible to obtain a good compromise between the column size and the number of separation stages to be used and the energy to be used to ensure this separation.
- The technical acrylic acid subjected to the process according to the invention contains a weight content of total aldehydes (furfural, benzaldehyde and acrolein) of less than 0.1%.
- The process according to the invention is carried out in continuous or semicontinuous mode, preferably in continuous mode.

DESCRIPTION OF THE FIGURES

Other characteristics and advantages of the invention will emerge more clearly on reading the detailed description which follows, with reference to appended FIGS. 1 and 2 which represent:

FIG. 1: block diagram of the process according to a first embodiment of the invention;

FIG. 2: block diagram of the process according to a second embodiment of the invention.

DETAILED DESCRIPTION OF THE INVENTION

Definitions

In the description which follows, the term "polymer grade" and the term "glacial" have the same meaning and indicate that acrylic acid meets criteria of high quality enabling its use in the manufacture of high molecular weight (meth)acrylic polymers.

The term "agent for chemical treatment of the aldehydes" or "chemical reagent for treating the aldehydes" means a chemical compound which forma, with the aldehydes, heavier reaction products which become more easily separable from acrylic acid by distillation.

The term "chemical treatment" is understood to mean the treatment carried out using an agent for chemical treatment of the aldehydes.

This type of treatment and the compounds which can be used are well known in the prior art, without the reactions or complexations used being fully identified. The objective of the mode of action is mainly to form reaction products which are heavier than the aldehydes to be treated.

This agent for chemical treatment of the aldehydes term excludes polymerization inhibitors which, although they may have a minor effect on the aldehydes, are generally introduced for the sole purpose of stabilizing streams containing acrylic derivatives relative to polymerization, it being possible for these polymerization inhibitors to be present in the acrylic acid subjected to the process according to the invention.

The term "light" describing the by-product compounds denotes the compounds whose boiling point is lower than that of acrylic acid under the working pressure considered, and by analogy, the term "heavy" denotes the compounds whose boiling point is above that of acrylic acid.

The term "external organic solvent" denotes any organic compound in which acrylic acid is soluble and the origin of which is external to the process, used as absorption, extraction or azeotropic distillation solvent.

The term "azeotropic solvent" denotes any organ is solvent which has the property of forming an azeotropic mixture with water.

The term "noncondensable" denotes compounds whose boiling point is below a temperature of 20° C. under atmospheric pressure.

Production of Polymer Grade Acrylic Acid According to the Invention

According to the invention, a polymer-grade acrylic acid can be obtained by a simple operation of distilling a technical acrylic acid, without requiring a chemical treatment of the aldehydes. This distillation operation can follow the various processes for manufacturing technical acrylic acid without solvent, described for example in documents EP 2 066 613, WO 2015/126704, WO 2008/033687, or using external solvents such as WO 2010/031949.

Furthermore, it has become apparent that this invention could be applied to acrylic acid produced from propylene and/or propane raw materials and also to acrylic acid derived from renewable raw materials.

The quality of the technical acrylic acid subjected, to the process according to the invention can be defined as follows (weight contents):
  Water<0.2%, preferably <0.05%, for example <0.01%
  Acetic acid<0.25%, preferably <0.10%, for example <0.05%
  Furfural<0.05%, preferably 0.03%, for example <0.005%
  Benzaldehyde<0.05%, preferably <0.02%, for example <0.005%
  Acrolein<0.02%, preferably <0.01%
  Protoanemonin<0.02%, preferably <0.01%, for example <0.005%.

According to the invention, said stream of technical acrylic acid is sent to a single distillation unit from which an acrylic acid stripped of most of the residual aldehydes is withdrawn as sidestream, which acrylic acid corresponds to the desired polymer or glacial grade defined as follows:
  purity greater than 99.5 wt %,
  less than 0.05 wt % water,
  less than 0.075% acetic acid,
  furfural content<2 ppm,
  benzaldehyde content<2 ppm,
  protoanemonin content<2 ppm,
  a weight content of total aldehydes<10 ppm.

The Distillation Unit

The process for manufacturing glacial acrylic acid from a technical acrylic acid comprising aldehyde compounds in a low content, consists of a distillation carried out in a single distillation unit which is devoid of a dividing-wall distillation column.

With reference to FIG. 1 which represents a first embodiment of the invention, the column E12 is equipped with a sidestream drawoff and comprises a number of theoretical plates of between 15 and 30, preferably between 20 and 25. This single column operates under a reduced pressure generally of between 20 mmHg and 150 mmHg, preferably between 30 mmHg and 100 mmHg.

Column E12 consists of any type of plates and/or random internals and/or structured packings available for the rectification of mixtures and suitable for the distillation of polymerizable compounds. It may be a conventional distillation column which may comprise at least one packing, for instance random packing and/or a combination of sections equipped with random and structured packings, and/or plates, for instance perforated plates, fixed valve plates, movable valve plates, bubble plates, or combinations thereof. Preferably, column E12 is equipped with perforated plates.

The stabilization of column E12 is generally carried out using stabilizers well known to those skilled in the art, optionally with injection of air or of oxygen-depleted air.

The column E12 is fed in the first quarter of the bottom of the column, preferably at a plate ranging from plates 2 to 7, preferably from plates 3 to 5.

In the absence of chemical treatment of the aldehydes, a gaseous fraction rich in light compounds, such as acrolein, acetic acid and water is distilled at the top of the column and removed after condensation and optionally additional treatment, or recycled upstream of the purification process, or used for the manufacture of acrylic esters. When a partial condensation is carried out, these uncondensed light compounds can be sent directly in gaseous form to a vent treatment unit.

The polymer-grade acrylic acid is withdrawn in the liquid phase or in the gas phase, preferably from the first third of the top of the column E12, in particular between the theoretical plates 1 to 5 plates located below the top of the column. Preferably, the polymer grade acrylic acid is withdrawn in the liquid phase.

At the bottom of column E12, an acrylic acid stream comprising most of the heavy impurities (in particular furfural, benzaldehyde, protoanemonin and non-phenolic inhibitors) separated from the acrylic acid stream feeding column E12, can be advantageously recycled as a technical grade of acrylic acid to an esterification unit, without additional purification.

The weight ratio between the stream withdrawn as a sidestream and the feed stream of column E12 is between 60% and 90%, preferably between 70% and 80%.

The weight ratio between the stream withdrawn as bottoms and the feed stream of column E12 is between 10% and 40%, preferably between 20% an 30%.

According to one particular embodiment, the column E12 is equipped with a condenser and a liquid feed at the top, which ensures liquid reflux in the column. The reflux ratio which can be defined as the rate of recycling from the top of the column to the column, relative to that of sidestream drawoff, is between 1.5 and 4, preferably between 2 and 3, for example is equal to 2.5. These conditions make it possible to lead to the best compromise between the size of the column/number of separation stages to be used and the energy to be used to ensure effective distillation.

The light compounds at the top of the column are removed preferentially in the gas phase after a partial condensation operation.

Referring to FIG. 2 which shows a second embodiment of the invention, the distillation unit comprises two distillation columns E1 and E2 fluidly connected to one another by the gas stream distilled at the top of the column E1 which feeds the bottom of column E2.

Each of the columns E1 and E2 comprises a number of theoretical plates of between 8 and 15, preferably between 10 and 12.

Columns E1 and E2 are generally conventional distillation columns which may comprise at least one packing, for instance random packing and/or structured packing, and/or plates, for instance perforated plates, fixed valve plates, movable valve plates, bubble plates, or combinations thereof. Preferably, columns E1 and E2 are equipped with perforated plates.

Columns E1 and E2 are generally stabilized with respect to polymerization using stabilizers well known to those skilled in the art, optionally with injection of air or of oxygen-depleted air.

Columns E1 and E2 operate under a reduced pressure generally of between 20 mmHg and 150 mmHg, preferably between 30 mmHg and 100 mmHg.

The column E1 is fed preferably in the first quarter of the bottom of the column, preferably at a plate ranging from plates 2 to 7, preferably from plates 3 to 5.

The gas phase generated at the top of column E1 feeds column E2 in the first quarter of the bottom of the column, preferably at a plate located ranging from plates 1 to 3 of this column.

In the absence of chemical treatment of the aldehydes, a gaseous fraction essentially entraining the light compounds, such as acrolein, acetic acid and water is distilled at the top of column E2, and recovered after condensation in order to be treated in a biological plant or, when only a partial condenser is used, these light compounds are sent directly to a vent treatment unit.

According to one embodiment, at least one portion of the stream condensed at the top of column E2 is sent as reflux to column E2 and consequently to column E1.

The reflux ratio which can be defined as the rate of recycling from the top of the column E2 to the column E2, relative to that of sidestream drawoff from column E2 is between 1.5 and 4, preferably between 2 and 3, for example is equal to 2.5. These conditions make it possible to lead to the best compromise between the size of the columns/ number of separation stages to be used and the energy to be used to ensure effective distillation.

The polymer-grade acrylic acid is withdrawn in the liquid phase or in the gas phase, preferably from the first third of the top of the column E2, in particular between the theoretical plates 1 to 5 plates below the top of the column. Preferably, the polymer-grade acrylic acid is withdrawn in the liquid phase. The weight ratio between the stream withdrawn as a sidestream from column E2 and the feed stream of column E1 is between 60% and 90%, preferably between 70% and 80%.

The weight ratio between the stream withdrawn at the bottom of column E1 and the feed stream of column E1 is between 10% and 40%, preferably between 20% and 30%. The bottom stream from column E2 is sent in liquid form to the top of column E1.

At the bottom of column E1, an acrylic acid stream comprising most of the heavy impurities (in particular furfural, benzaldehyde, protoanemonin and non-phenolic inhibitors) separated from the acrylic acid stream feeding column E1, can be advantageously recycled as a technical grade acrylic acid to an esterification unit, without additional purification.

The energy consumption in the process according to the invention is generally higher than that required in a separation using hydrazine or derivatives thereof for treating the aldehydes. This additional energy cost is however largely offset by the gain obtained due to the absence of production shutdowns and cleaning and maintenance operations following fouling linked to the use of an amino compound, and above all by the absence of a CMR product and its restrictive industrial environment.

The invention will now be illustrated by the following examples, which do not have the aim of limiting the scope of the invention, defined by the appended claims.

EXPERIMENTAL SECTION

The percentages are expressed as weight percentages,
The following abbreviations are used in the tables:
AA: acrylic acid
ACO: acrolein
ACOH: acetic acid
Furfural: furfuraldehyde
Benzal: Benzaldehyde
PTA: protoanemonin
HZ: hydrazine hydrate Simulations using thermodynamic models and ASPEN software were used to illustrate a process according to the prior art and the process according to the invention. Protoanemonin does not appear in these examples because this impurity is unstable and is not described in the existing thermodynamic models. However, the experimental distillation of a mixture of acrylic acid containing the impurities furfural (120 ppm), benzaldehyde (80 ppm) and protoanemonin (50 ppm) shows that the volatility of protoanemonin is between that of benzaldehyde (the least volatile compound) and that of furfuraldehyde (the most volatile compound). Thus, it can be concluded that the concentrations of protoanemonin are necessarily lower than those of furfuraldehyde (well described in thermodynamic models).

Example 1 (Comparative)

According to a prior art process, a stream of technical grade acrylic acid is subjected to a distillation operation using two columns E3 and E4 in series in the presence of hydrazine hydrate.

The first column E3 (with 12 theoretical stages, and operating under a pressure of 45 mmHg) is fed by the stream of acrylic acid to be purified and hydrazine as an amino compound reacting with the aldehydes, at theoretical plate 3 counted from the bottom of the column. At the top of column E3 (topping column), light impurities such as water generated during the reaction of hydrazine with aldehyde impurities and acetic acid are removed. The mass reflux ratio of this column/distillate flow rate is set between 0.5 and 0.7.

The bottom stream from the topping column E3 feeds a second distillation column E4 (with 12 theoretical stages and operating under a pressure of 8500 Pa). Column E4 carries out, at the top, the distillation of the purified acrylic acid, and, at the bottom, the removal of the heavy compounds, comprising in particular the reaction products of hydrazine with aldehyde impurities and with acrylic acid (excess reagent). This column is fed under the first plate at the bottom of the column.

Table 1 below collates the weight composition of the various streams.

TABLE 1

| | Technical AA | Column E3 feed after HZ addition | Bottom of column E3 | Top of column E3 | Top of column E4 | Bottom of column E4 |
|---|---|---|---|---|---|---|
| Flow rate, kg/h | 22525 | 22712 | 18905 | 4001 | 17510 | 2005 |
| AA | 0.997048 | 0.9963911 | 0.9961708 | 0.9930293 | 0.99895 | 0.9303336 |
| WATER | 5.31E−04 | 9.89E−04 | 4.64E−11 | 5.54E−03 | 4.97E−11 | 6.09E−13 |
| ACO | 7.58E−05 | 6.47E−05 | 0 | 3.61E−04 | 0 | 0 |
| ACOH | 6.63E−04 | 6.58E−04 | 6.13E−04 | 8.35E−04 | 6.16E−04 | 3.99E−04 |
| FURFURAL | 1.44E−04 | 2.15E−06 | 2.49E−06 | 4.36E−07 | 1.28E−06 | 1.23E−05 |
| BENZAL | 6.91E−05 | 6.17E−06 | 7.35E−06 | 2.97E−07 | 2.16E−07 | 6.74E−05 |

According to this process carried out in the presence of hydrazine hydrate, acrylic acid meeting the specifications of a polymer grade is obtained at the top of the second column E4, in a proportion of 17.510 kg per 22.525 kg of technical acrylic acid supplied. The overall energy cost for the operation of the 2 columns has been estimated at 4.54 Gcal/h. The content of acrylic acid is 99.9% and the impurities furfuraldehyde, benzaldehyde and acrolein are present in a content of less than 1 ppm. The stream from the bottom of column E4 contains the compounds resulting from the reaction of hydrazine with aldehydes and from side reactions with acrylic acid. This stream rich in acrylic acid is unsuitable for the manufacture of esters.

Example 2 (Comparative)

The configuration of the process of example 1 is used, but no addition of hydrazine hydrate is carried out.

Table 2 below collates the weight composition of the various streams.

TABLE 2

| Technical AA | Bottom of column E3 | Top of column E3 | Top of column E4 | Bottom of column E4 |
|---|---|---|---|---|
| 22525 | 18921 | 4002 | 17526 | 2005 |
| 0.997048 | 0.9950177 | 0.9943221 | 0.9986099 | 0.9225428 |
| 5.31E−04 | 3.68E−11 | 4.05E−03 | 3.94E−11 | 4.88E−13 |
| 7.58E−05 | 0 | 4.20E−04 | 0 | 0 |
| 6.63E−04 | 6.13E−04 | 8.34E−04 | 6.16E−04 | 4.01E−04 |
| 1.44E−04 | 1.66E−04 | 2.92E−05 | 8.48E−05 | 8.21E−04 |
| 6.91E−05 | 8.16E−05 | 3.31E−06 | 2.39E−06 | 7.49E−04 |

In the configuration of the process according to the prior art, in the absence of amino reagent, the acrylic acid distilled at the top of the second column does not meet the specifications of a polymer grade for the residual aldehydes, in particular for the furfural which has a content of 85 ppm for a specification of less than 5 ppm.

Example 3 (According to the Invention)

A configuration as represented in FIG. 1 is used for the simulation of the process according to the invention.

Column E12 comprises 24 theoretical plates and it is equipped at the top with a partial condenser and a sidestream drawoff at plate no. 5 counted from the column top. Column E12 is fed with a stream of technical acrylic acid, without addition of an aldehyde treatment agent. The column operates under a pressure of 100 mmHg. The temperature at the sidestream drawoff is 90° C., and that at the bottom is 111° C.

Table 3 below collates the weight composition of the various streams.

TABLE 3

| | E12 Feed | Top of column E12, gas phase | Top of column E12 liquid phase | Bottom of column E12 | E12 Sidestream drawoff |
|---|---|---|---|---|---|
| Flow rate, kg/h | 22529 | 1072 | 43 | 5008 | 17521 |
| AA | 0.99612 | 0.80162 | 0.99612 | 0.98524 | 0.9991 |
| WATER | 5.3E−04 | 1.08E−02 | 1.42E−03 | 0 | 1.48E−05 |
| ACO | 7.58E−05 | 1.57E−03 | 8.40E−05 | 0 | 1.03E−06 |
| ACOH | 6.62E−04 | 6.69E−04 | 1.17E−03 | 1.12E−04 | 7.75E−04 |
| FURFURAL | 1.44E−04 | 4.97E−08 | 1.74E−07 | 6.44E−04 | 9.95E−07 |
| BENZAL | 6.9E−05 | 0 | 0 | 3.10E−04 | 0 |

The stream withdrawn as sidestream corresponds to a polymer grade acrylic acid. For the same production as that obtained in the conventional process of example 1, the energy consumption in this configuration is 7.15 Gcal/h at the boiler. This overconsumption of energy is offset by the gain obtained due to the absence of production shutdowns and cleaning operations following fouling linked to the use of an amino compound, and due to the savings made in terms of investment in production equipment and the maintenance thereof (columns, exchangers, pumps, filters).

Moreover, the stream of acrylic acid recovered at the bottom of column E12, free from the reaction products of the aldehydes with an amino compound such as hydrazine, can be upgraded directly to an esterification unit without requiring additional purification.

The invention claimed is:

1. A process for manufacturing glacial acrylic acid from a technical acrylic acid comprising aldehyde compounds in a low content obtained by a purification process with or without external solvent, said process consisting of the step of:

distilling technical acrylic acid in an additional distillation unit in the absence of chemical reagent for treating the aldehydes, to produce
- a stream of polymer-grade acrylic acid which is withdrawn through a side outlet of the distillation unit,
- a stream comprising essentially light compounds which is extracted at the top of the distillation unit, and
- a stream of technical acrylic acid comprising heavy compounds which is recovered at the bottom of the distillation unit, wherein the stream recovered at the bottom of the distillation unit is recycled to an esterification unit without additional treatment.

2. The process as claimed in claim 1, wherein the distillation unit comprises a single distillation column E12 equipped with a sidestream drawoff which comprises a number of theoretical plates of between 15 and 30.

3. The process as claimed in claim 1, wherein the distillation unit comprises a first distillation column E1, in which the stream generated at the top feeds a second distillation column E2 equipped with a sidestream drawoff, each of the columns E1 and E2 comprising a number of theoretical plates of between 8 and 15.

4. The process as claimed in claim 1, wherein the distillation unit comprises at least one top reflux.

5. The process as claimed in claim 1, wherein the distillation unit comprises, at the top, a condenser which is a complete or partial condenser.

6. The process as claimed in claim 1, wherein the acrylic acid is of petrochemical origin.

7. The process as claimed in claim 1, wherein the acrylic acid is at least partly of renewable origin.

8. The process as claimed in claim 1, wherein the acrylic acid derives from a purification process comprising the extraction of acrylic acid by countercurrent absorption in the form of an aqueous solution of acrylic acid.

9. The process as claimed in claim 1, wherein the acrylic acid derives from a purification process comprising the extraction of acrylic acid by countercurrent absorption using a heavy hydrophobic solvent.

10. The process as claimed in claim 1, wherein the acrylic acid derives from a purification process without an external organic solvent.

* * * * *